United States Patent
Lim et al.

(10) Patent No.: US 9,833,516 B2
(45) Date of Patent: Dec. 5, 2017

(54) LIQUID FORMULATION OF LONG-ACTING INSULIN AND INSULINOTROPIC PEPTIDE

(71) Applicant: HANMI PHARM. CO., LTD., Hwaseong-si, Gyeonggi-do (KR)

(72) Inventors: Hyung Kyu Lim, Hwaseong-si (KR); Hyun Uk Kim, Busan (KR); Mi Kyoung Lee, Seoul (KR); Jong Soo Lee, Seongnam-si (KR); Sung Min Bae, Seongnam-si (KR); Se Chang Kwon, Seoul (KR)

(73) Assignee: HANMI PHARM. CO., LTD, Hwaseong-Si (KR)

( * ) Notice: Subject to any disclaimer, the term of this patent is extended or adjusted under 35 U.S.C. 154(b) by 0 days.

(21) Appl. No.: 14/416,231

(22) PCT Filed: Jul. 25, 2013

(86) PCT No.: PCT/KR2013/006676
§ 371 (c)(1),
(2) Date: Jan. 21, 2015

(87) PCT Pub. No.: WO2014/017849
PCT Pub. Date: Jan. 30, 2014

(65) Prior Publication Data
US 2015/0190528 A1 Jul. 9, 2015

(30) Foreign Application Priority Data
Jul. 25, 2012 (KR) .................. 10-2012-0081478

(51) Int. Cl.
| | | |
|---|---|---|
| A61K 39/00 | (2006.01) | |
| A61K 38/28 | (2006.01) | |
| A61K 38/26 | (2006.01) | |
| A61K 47/48 | (2006.01) | |
| A61K 38/22 | (2006.01) | |
| A61K 47/02 | (2006.01) | |
| A61K 47/10 | (2017.01) | |
| A61K 47/12 | (2006.01) | |
| A61K 47/22 | (2006.01) | |

(52) U.S. Cl.
CPC ........ *A61K 47/48415* (2013.01); *A61K 38/22* (2013.01); *A61K 38/26* (2013.01); *A61K 38/28* (2013.01); *A61K 47/02* (2013.01); *A61K 47/10* (2013.01); *A61K 47/12* (2013.01); *A61K 47/22* (2013.01); *A61K 47/48369* (2013.01)

(58) Field of Classification Search
CPC ......... A61K 38/26; A61K 47/10; A61K 47/48
See application file for complete search history.

(56) References Cited

U.S. PATENT DOCUMENTS

| | | | |
|---|---|---|---|
| 5,424,286 A | 6/1995 | Eng | |
| 8,476,230 B2 * | 7/2013 | Song | C07K 14/605 424/195.11 |
| 2003/0104996 A1 * | 6/2003 | Li | A61K 38/1816 514/7.7 |
| 2009/0238838 A1 | 9/2009 | Kim et al. | |
| 2010/0105877 A1 * | 4/2010 | Song | C07K 14/605 530/391.9 |
| 2011/0257091 A1 * | 10/2011 | DiMarchi | C07K 14/62 514/6.2 |
| 2012/0283179 A1 | 11/2012 | Brunner-Schwarz et al. | |
| 2013/0028918 A1 | 1/2013 | Song et al. | |

FOREIGN PATENT DOCUMENTS

| | | |
|---|---|---|
| CN | 102319422 A | 1/2012 |
| JP | 2007-510675 A | 4/2007 |
| JP | 2008-519807 A | 6/2008 |
| KR | 10-0725315 B1 | 6/2007 |
| KR | 10-2009-0008151 A | 1/2009 |
| KR | 10-1058290 B1 | 8/2011 |
| KR | 10-2011-0111267 A | 10/2011 |
| KR | 10-2011-0134209 A | 12/2011 |
| KR | 10-2011-0134210 A | 12/2011 |
| KR | 10-2012-0135123 A | 12/2012 |
| RU | 2 354 366 | 9/2006 |
| RU | 2 436 589 | 2/2011 |
| WO | 96/32478 A1 | 10/1996 |
| WO | 97/34631 A1 | 9/1997 |
| WO | 2005/046716 A1 | 5/2005 |

(Continued)

OTHER PUBLICATIONS

State Intellectual Property Office of the P.R.C., Communication dated Jan. 20, 2016, issued in corresponding Chinese Application No. 201380039763.0.
European Patent Office, Communication dated Feb. 29, 2016, issued in counterpart European Application No. 13822545.3.
Kumar M et al: "Gene therapy of diabetes using a novel GLP-1/IgG1-Fc fusion construct normalizes glucose levels in db/db mice", Gene Therapy, Nature Publishing Group, GB, vol. 14, No. 2, Jan. 1, 2007 (Jan. 1, 2007), pp. 162-172, XP002499114 ISSN: 0969-7128.
Communication dated May 29, 2017 from the Japanese Patent Office in counterpart application No. 2015-524185.
Qinghua Wang et al., "Novel GLP-1 Fusion Chimera as Potent Long Acting GLP-1 Receptor Agonist," PLoS One, Sep. 2010, pp. 1-9, vol. 5, Issue 9.
William R Strohl, "Optimization of Fc-mediated effector functions of monoclonal antibodies," Current Opinion in Biotechnology, 2009, pp. 685-691, vol. 20, No. 6.

(Continued)

*Primary Examiner* — Gyan Chandra
(74) *Attorney, Agent, or Firm* — Sughrue Mion, PLLC (57) ABSTRACT

The present invention relates to a liquid formulation of a combination of long-acting insulin and insulinotropic peptide, comprising insulin which is a physiologically active peptide, insulinotropic peptide, and albumin-free stabilizer, wherein the stabilizer comprises a buffer, a sugar alcohol, a non-ionic surfactant, and an isotonic agent; and a method for preparing the liquid formulation. The liquid formulation of the present invention does not contain a human serum albumin and potentially toxic factors to the body, and thus it has excellent storage stability for insulin conjugate and insulinotropic peptide conjugate at high concentration, without a risk of viral contamination.

30 Claims, 4 Drawing Sheets

(56) References Cited

FOREIGN PATENT DOCUMENTS

| WO | 2006/051103 A2 | 5/2006 |
| WO | 2011/058082 A1 | 5/2011 |
| WO | 2011/090305 A2 | 7/2011 |
| WO | 2011/090306 A2 | 7/2011 |
| WO | 2011122921 A2 | 10/2011 |
| WO | 2011/144673 A2 | 11/2011 |
| WO | 2012/008779 A2 | 1/2012 |
| WO | 2012/057525 A2 | 5/2012 |

OTHER PUBLICATIONS

International Searching Authority, International Search Report of PCT/KR2013/006676 dated Oct. 21, 2013.
International Searching Authority, Written Opinion of the International Searching Authority of PCT/KR2013/006676 dated Oct. 21, 2013.
Russian Patent Office, Communication dated Jul. 24, 2017 by the Russian Patent Office in counterpart Russian Patent Application No. 2015104489/15(007044).

* cited by examiner

[Figure 1]

duration of the absence of protein precipitation (in days)

※¹ #1 (20mM Na-Citrate, pH5.6)
: protein precipitation within 1 week
※² #2 (20mM Na-Citrate, pH5.6, 10mg/mL NaCl)
: protein precipitation after 1 week

※¹  Control-1(long-acting insulinotropic peptide conjugate)
    : protein precipitation after 2 weeks
※²  #1 (20mM Na-Citrate, pH5.6)
    : protein precipitation within 1 week
※³  #2 (20mM Na-Citrate, pH5.6, 10mg/mL NaCl)
    : protein precipitation after 1 week

[Figure 4]

SEQUENCE LISTING

```
<160> NUMBER OF SEQ ID NOS: 5

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
 1               5                  10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic construct of GLP-1(7-37)

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30
```

```
<210> SEQ ID NO 4
<211> LENGTH: 39
<212> TYPE: PRT
<213> ORGANISM: Artificial Sequence
<220> FEATURE:
<223> OTHER INFORMATION: Synthetic construct of exendin-3

<400> SEQUENCE: 4

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic construct of exendin-4

<400> SEQUENCE: 5

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35
```

LIQUID FORMULATION OF LONG-ACTING INSULIN AND INSULINOTROPIC PEPTIDE

CROSS REFERENCE TO RELATED APPLICATIONS

This is a National Stage of International Application No. PCT/KR2013/006676 filed Jul. 25, 2013, claiming priority based on Korean Patent Application No. 10-2012-0081478 filed Jul. 25, 2012, the contents of all of which are incorporated herein by reference in their entirety.

TECHNICAL FIELD

The present invention relates to a liquid formulation of a combination of long-acting insulin and insulinotropic peptide, comprising insulin and insulinotropic peptide which are physiologically active peptides, and albumin-free stabilizer, wherein the stabilizer comprises a buffer, a sugar alcohol, a non-ionic surfactant, and an isotonic agent; and a method for preparing the liquid formulation.

BACKGROUND ART

Insulin is a peptide secreted by pancreatic beta cells, and plays a central role in the control of blood glucose in the body. If the amount of insulin secreted is lacking or the secreted insulin does not function properly in the body, the blood glucose level will be elevated, causing metabolic disease called diabetes. When the insulin is not secreted properly or does not function properly in the body, the blood glucose level is increased without regulation, and this type of diabetes is called type II diabetes. Type I diabetes is caused when the pancreas does not make enough insulin to regulate the increase of blood glucose. Type II diabetes is usually treated by administering oral hypoglycemic agents which mainly consist of chemical compounds, and sometimes insulin may be administered to some of the patients. On the other hand, for treating type I diabetes, administration of insulin is essential.

The widely-used insulin treatment is an injection of insulin before and after meals. Insulin is currently available in a formulation for parenteral injection and administered subcutaneously in principle, and depending on the duration of treatment, a method of administration is different. Administration of insulin by injection is more effective in reducing blood glucose level compared to the oral medicine, and it can be safely applied in the circumstances when an oral drug cannot be used. Also, parenteral injection of insulin does not have a limitation of dose, however since it has to be continuously administered three times a day, it has disadvantages such as causing an aversion to needles, difficult administration method, symptoms of hypoglycemia, and symptoms of weight gain due to prolonged insulin administration. Especially, the weight gain increases a risk of developing cardiovascular diseases and may disrupt the regulatory function of body for blood glucose level. Meanwhile, there have been many attempts to maximize the therapeutic effect of an insulin peptide drug by maintaining a high drug level in blood for a long period of time, after administering the drug into the body. As a result, long-acting insulin has been developed, manufactured, and commercialized. Examples of such long-acting drug include Lantus (insulin glargine; Sanofi Aventis) and Levemir (insulin detemir; Novo Nordisk). Unlike neutral protamine Hagedorn (NPH) insulin, the long-acting drugs have a lower risk of hypoglycemia during hypnoidal state. In particular, Levemir alleviates the symptom of weight gain. However, the administration method involving one or two injections per day is still remained as a disadvantage.

Meanwhile, a glucagon-like-peptide-1 (GLP-1), which is a type of insulinotropic peptide, is an incretin hormone secreted from L-cell of ileum and large intestine. The main function of GLP-1 is to increase the secretion of insulin for establishing a glucose-dependent insulin secretion in the body, thereby preventing hypoglycemia. With this effect, GLP-1 can be applied to treat type 2 diabetes. However as the serum half-life of GLP-1 is as short as 2 minutes, it has high limitation to be developed into a drug. Accordingly, a new GLP-1 agonist called exendin-4 has been developed and manufactured. Exendin-4 is a GLP-1 agonist produced in the salivary gland of Glia monster lizard. Furthermore, exendin-4 is resistant to dipeptidyl peptidase-4 (DPP-IV) and has a higher physiological activity than GLP-1. Thus, exendin-4 has 2 to 4 hour-long half-life in the body, which is a lot longer than that of GLP-1 (U.S. Pat. No. 5,424,286). However, a sufficient duration of physiological activity of drug cannot be achieved merely by increasing resistance to DPPIV. For instance, the currently available exendin-4 (exenatide) has to be administered twice a day to the patient by injection, and it still has disadvantages of causing vomiting and nausea.

Therefore, as a method to maintain the activity of protein drug and improve the stability thereof in the body simultaneously for resolving the above problems, the present inventors have previously suggested a development of long-acting protein conjugate by linking a known physiologically active polypeptide and immunoglobulin Fc region through covalent bonding by using a non-peptidyl polymer as a linker (Korean Patent Registration No. 10-0725315). In particular, it was previously confirmed that each of long-acting insulin conjugate and long-acting exendin-4 conjugate has remarkably increased in vivo durability (Korean Patent Registration No. 10-1058290 and Publication No. 10-2011-0134210). However, if a therapeutically effective amount of insulin or exendin-4 is administered for maintaining a stable blood glucose level; this may cause weight gain or symptoms of vomiting and nausea. Therefore, there is a high demand for developing a therapeutic method that can reduce a dosage of drug and frequency while providing excellent therapeutic effect for diabetes.

DISCLOSURE

Technical Problem

Given this background, in effort to provide a stable liquid formulation of a combination of long-acting insulin conjugate and long-acting insulinotropic peptide conjugate, which can store the combination of the two conjugates without a risk of viral contamination for a long period of time, the present inventors have enhanced the stability of the combination of the two conjugates by using a stabilizer comprising a buffer, a sugar alcohol, sodium chloride as an isotonic agent, and a non-ionic surfactant, and developed a cost-effective and stable liquid formulation, thereby completing the present invention.

Technical Solution

One object of the present invention is to provide a liquid formulation of a combination of long-acting insulin and insulinotropic peptide, comprising insulin and insulinotropic peptide which are physiologically active peptides, and an albumin-free stabilizer, wherein the stabilizer comprises a buffer, a sugar alcohol, a non-ionic surfactant, and an isotonic agent.

Another object of the present invention is to provide a method for preparing the liquid formulation.

Another object of the present invention is to provide a pharmaceutical composition for preventing or treating diabetes, comprising insulin and insulinotropic peptide.

Another object of the present invention is to provide a method for treating diabetes, comprising administering the composition to a subject having diabetes.

Advantageous Effects

The combination of long-acting insulin conjugate and long-acting insulinotropic peptide conjugate of the present invent ion shows excellent therapeutic effect for treating diabetes. Furthermore, a liquid formulation of a combination of long-acting insulin conjugate and long-acting insulinotropic peptide conjugate of the present invention comprises a stabilizer comprising a buffer, a sugar alcohol, an isotonic agent, and a non-ionic surfactant, but does not contain human serum albumin and other potentially toxic factors to body, and thus it does not have a risk of viral contamination. Also, the liquid formulation provides excellent storage stability for the long-acting insulin conjugate and long-acting insulinotropic peptide conjugate which have larger molecular weight and increased in vivo durability compared to a native form, through being composed of insulin or insulinotropic peptide and immunoglobulin Fc region. In particular, the present invention provides a stable liquid formulation for a combination of the long-acting insulin conjugate and long-acting insulinotropic peptide conjugate. Such liquid formulation of the present invention is a simple formulation providing excellent storage stability, and thus it is more cost-effective compared to other stabilizer or freeze-dried formulation. Also, the present liquid formulation can maintain the protein activity in the body for a long period of time, compared to other conventional formulations of insulin and insulinotropic peptide, and thus it can be used as an effective drug formulation.

Best Mode

As one aspect of the present invention provides a liquid formulation of a combination of long-acting insulin and insulinotropic peptide, comprising insulin and insulinotropic peptide, which are physiologically active peptides, and an albumin-free stabilizer, wherein the stabilizer comprises a buffer, a sugar alcohol, a non-ionic surfactant, and an isotonic agent. The liquid formulation of the present invention is characterized in that insulin and insulinotropic peptide are co-administered.

The insulin may be comprised in a liquid formulation in a form of a pharmaceutically effective amount of long-acting insulin conjugate, wherein the insulin is linked to an immunoglobulin Fc region. The insulinotropic peptide may be comprised in a liquid formulation in a form of a pharmaceutically effective amount of long-acting insulinotropic peptide conjugate, wherein the insulinotropic peptide is linked to an immunoglobulin Fc region.

As used herein, "long-acting insulin conjugate" refers to a conjugate wherein a physiologically active insulin, which includes derivative, variant, precursor, and fragment, is linked with an immunoglobulin Fc region, and it may refer to a conjugate having increased in vivo duration of physiological activity compared to a native insulin. As used herein, long-acting insulin conjugate refers to the insulin linked with an immunoglobulin Fc region through a non-peptidyl linker or peptidyl linker. As used herein, "long-acting insulinotropic peptide conjugate" refers to a conjugate, wherein a physiologically active insulinotropic peptide, which includes a derivative, variant, precursor, and fragment, is linked with an immunoglobulin Fc region, and it may refer to a conjugate having increased in vivo duration of physiological activity compared to native insulinotropic peptide.

As used herein, long-acting insulinotropic peptide conjugate refers to the insulinotropic peptide linked to an immunoglobulin Fc region through a non-peptidyl linker or peptide linker.

As used herein, the term "long-acting" refers to an enhancement of duration of physiological activity compared to that of a native peptide. The term "conjugate" refers to a form of peptide, wherein insulin or insulinotropic peptide is linked with an immunoglobulin Fc region.

The long-acting insulin conjugate or insulinotropic peptide conjugate of the present invention has an enhanced durability of effect compared to native insulin or insulinotropic peptide. The type of the long-acting insulin conjugate or insulinotropic peptide conjugate includes a form of insulin or insulinotropic peptide generated by modification, substitution, addition, or deletion of amino acids from a native insulin or insulinotropic peptide; a conjugate wherein insulin or insulinotropic peptide is linked with a biodegradable polymer such as PEG; a conjugate wherein insulin or insulinotropic peptide is linked with a protein with high durability such as albumin or immunoglobulin; a conjugate wherein insulin or insulinotropic peptide is linked with a fatty acid which has a binding affinity with albumin in the body; or a form of insulin or insulinotropic peptide which is enclosed in a biodegradable nano-particle, but is not limited thereto.

The long-acting insulin or insulinotropic peptide conjugate used in the present invention is prepared by linking the synthesized insulin or insulinotropic peptide with an immunoglobulin Fc region. The method for linking the two may be cross-linking insulin or insulinotropic peptide with an immunoglobulin Fc region via a non-peptidyl polymer, or by the production of a fusion protein in which insulin or insulinotropic peptide and an immunoglobulin Fc region are linked by genetic recombination.

As used herein, "insulin" refers to a peptide that is secreted by pancreas in response to the elevated blood glucose levels in the body to take up glucose into the liver, muscle, or adipose tissue turn it into glycogen, and to stop the use of fat as an energy source, and thus functions to control blood glucose. This peptide includes native insulin, basal insulin, and the agonists, precursors, derivatives, fragments, and variants thereof.

As used herein, "native insulin" is a hormone that is secreted by pancreas to promote glucose absorption but inhibit fat breakdown in the cells and thus functions to control the blood glucose level. Insulin is generated by processing its precursor, proinsulin, which does not have a function of regulating blood glucose level. The amino acid sequences of insulin are as follows:

```
Alpha chain:
                                        (SEQ ID NO. 1)
Gly-Ile-Val-Glu-Gln-Cys-Cys-Thr-Ser-Ile-Cys-Ser-
Leu-Tyr-Gln-Leu-Glu-Asn-Tyr-Cys-Asn Beta chain:
                                        (SEQ ID NO. 2)
Phe-Val-Asn-Gln-His-Leu-Cys-Gly-Ser-His-Leu-Val-
Glu-Ala-Leu-Tyr-Leu-Val-Cys-Gly-Glu-Arg-Gly-Phe-
Phe-Tyr-Thr-Pro-Lys-Thr
```

As used herein, "basal insulin" refers to a peptide regulating normal blood glucose level changes during each day, and examples of such peptide include levemir, lantus, and degludec. As used herein, "insulin agonist" refers to a compound that binds to the intrinsic receptor of insulin, showing the same biological activity as insulin, regardless of the structural difference to insulin. As used herein, "insulin variant" refers to a peptide having one or more different amino acid sequences from the native insulin, which has a function of regulating the blood glucose level in the body. The insulin derivative may be prepared by one of substitution, addition, deletion, and modification of some amino acids from native insulin or a combination thereof. As used herein, "insulin derivative" refers to a peptide having at least 80% amino acid sequence homology with the native insulin, which may have some groups on the amino acid residue chemically substituted (e.g., alpha-methylation, alpha-hydroxylation), deleted (e.g., deamination), or modified (e.g., N-methylation), and has a function of regulating the blood glucose level in the body. As used herein, "insulin fragment" refers to a fragment having one or more amino acids added or deleted at the N-terminal or the C-terminal of native insulin, wherein non-naturally occurring amino acids (e.g., D-type amino acid) may be added. The insulin fragment has a function of regulating the blood glucose level in the body.

Each of the methods used for preparing the agonists, derivatives, fragments, and variants of insulin can be applied individually or in combination. For example, the scope of the present invention comprises a peptide that has one or more amino acid sequences different from those of native peptide and has the N-terminal amino acid residue deaminated, while possessing a function of regulating the blood glucose level in the body.

The insulin used in the present invention may be produced by a recombination technology or synthesized by a solid phase synthesis. Also, the insulin used in the present invention may be linked with a non-peptidyl polymer. Such non-peptidyl polymer can be used as a linker in the present invention. By linking insulin with the non-peptidyl polymer as a linker, the stability of insulin can be improved while maintaining the activity thereof. A peptide may be applied as a linker by using a genetic recombination technique.

As used herein, "non-peptidyl polymer" refers to a biocompatible polymer composed of one or more repeating units, wherein the repeating units are linked to each other through any type of covalent bond, but not by a peptide bond. In the present invention, the "non-peptidyl polymer" can be used interchangeably with "non-peptidyl linker".

The non-peptidyl polymer which can be used in the present invention is selected from the group consisting of biodegradable polymers such as polyethylene glycol, polypropylene glycol, copolymers of ethylene glycol and propylene glycol, polyoxyethylated polyols, polyvinyl alcohol, polysaccharides, dextran, polyvinyl ethyl ether, polylactic acid (PLA), and polylactic-glycolic acid (PLGA); lipid polymers; chitins; hyaluronic acid; and a combination thereof. Preferably, polyethylene glycol is used as the non-peptidyl polymer. The scope of the present invention also includes the derivatives thereof that are well-known in the art and the derivatives that can be easily prepared by using the techniques available in the art.

The peptidyl linker used in a fusion protein, which is prepared by a conventional inframe fusion method, has a limitation in that it can be easily cleaved by a protease in the body, and thus it cannot increase the serum half-life of active drug sufficiently as much as when a carrier is used. However, in the present invention, the serum half-life of the peptide can be maintained at a similar level to that when a carrier is used, by using a polymer resistant to the protease. Therefore, the non-peptidyl polymer that can be used in the present invention includes any type of non-peptidyl polymers, as long as it has the aforementioned function, that is, being resistant to protease. The non-peptidyl polymer has a molecular weight of 1 to 100 kDa, and preferably 1 to 20 kDa. Also, the non-peptidyl polymer of the present invention, which is linked to an immunoglobulin Fc region, may be a single type of polymers or a combination of different types of polymers.

The non-peptidyl polymer used in the present invention may have a functional group that can be linked to an immunoglobulin Fc region and protein drug. The functional groups of the non-peptidyl polymer at both terminals are preferably selected from the group consisting of a reactive aldehyde group, a propionaldehyde group, a butyl aldehyde group, a maleimide group, and a succinimide derivative. The succinimide derivative may be succinimidyl propionate, hydroxy succinimidyl, succinimidyl carboxymethyl, or succinimidyl carbonate. In particular, when the non-peptidyl polymer has reactive aldehyde groups at both terminals, this can minimize the non-specific bindings and can make effective linking of the non-peptidyl polymer with a physiologically active polypeptide and an immunoglobulin at each end. A final product generated by reductive alkylation forming aldehyde bond is much more stable than those linked by an amide bond. An aldehyde functional group selectively binds to the N-terminal at low pH, and forms a covalent bond with a lysine residue at high pH, for example at a pH of 9.0.

The functional groups at two terminals of the non-peptidyl polymer may be the same or different. For example, the non-peptidyl polymer may have a maleimide group at one terminal, and an aldehyde group, a propionaldehyde group or a butyl aldehyde group at the other terminal. When a polyethylene glycol having a hydroxy group at both terminals is used as a non-peptidyl polymer, the hydroxy group may be activated into various functional groups by known chemical reactions, or a commercially available polyethylene glycol having modified functional group may be used so as to prepare the long-acting insulin conjugate of the present invention.

Preferably, the non-peptidyl polymer may be linked to the N-terminal of beta-chain of insulin.

The insulin of the present invention may be modified with a non-peptidyl polymer.

When developing a long-acting insulin conjugate by using an immunoglobulin fragment, if a physiologically active polypeptide is modified with PEG for increasing the durability of drug without causing hypoglycemia, this may reduce titer. However, the reduction of titer becomes an advantage of the long-acting insulin conjugate and thus the insulin modified with PEG can be combined with immunoglobulin Fc region through a non-peptidyl polymer. The type of non-peptidyl polymer that can be used in modification of insulin is the same as described above, and preferably polyethylene glycol (PEG). In the PEG-modified insulin, the PEG is selectively linked to the N-terminal of alpha-chain of insulin or to a specific lysine residue of beta-chain. PEG that modifies the insulin preferably comprises an aldehyde group or a succinyl group at the terminal, and more preferably a succinyl group.

The preparation method and effect of the long-acting insulin conjugate of the present invention are disclosed in Korean Patent Publication Nos. 10-2011-0134210, 10-2011-0134209, and 10-2011-0111267. Those skilled in the art can prepare the long-acting insulin conjugate used in the present invention by referring to these references. Also, the present inventors have previously found a method for preparing the long-acting insulin conjugate by mono-PEGylation of the N-terminal of immunoglobulin Fc region, and attaching the same to the first phenylalanine of beta-chain of insulin.

As used herein, "insulinotropic peptide" refers to a peptide having a function of secreting insulin, and it can stimulate the synthesis or expression of insulin in pancreatic β-cells. The insulinotropic peptide is preferably a glucagon like peptide-1 (GLP-1), GLP-2, exendin-3, or exendin-4, but is not limited thereto. The insulinotropic peptide includes a native insulinotropic peptide, as well as the precursors, agonist, derivatives, fragments, and variants thereof.

A derivative of the insulinotropic peptide of the present invention may refer to a derivative generated by deleting the N-terminal amino group (or amine group) of the insulinotropic peptide (i.e., desamino-histidyl derivative); a derivative generated by substituting an amino group of the insulinotropic peptide by hydroxyl group (i.e., beta-hydroxy imidazopropionyl derivative); a derivative generated by modifying the amino group of the insulinotropic peptide with two methyl groups (i.e., dimethyl-histidyl derivative); a derivative generated by substituting the amino group of N-terminal of insulinotropic peptide by carboxyl group (i.e., betacarboxyimidazopropionyl derivative); or a derivative generated by removing the positive charge of amino group of insulinotropic peptide by deleting the alpha-carbon of the N-terminal histidine residue, leaving an imidazoacetyl group only (imidazoacetyl derivative). In addition, the scope of the present invention includes other forms of N-terminal amino group-modified derivatives.

In the present invention, the insulinotropic peptide derivative is preferably a derivative generated by chemical modification of the N-terminal amino group or amino acid residue of exendin-4, and more preferably an exendin-4 derivative where alpha-amino group or alpha-carbon group present in the alpha-carbon of histidine residue, which is the first amino acid of the N-terminal of exendin-4, is substituted or deleted. Even more preferably, the insulinotropic peptide derivative is a desamino-histidylexendin-4 (DA-exendin-4) which is generated by deleting the N-terminal amino group of exendin-4; a beta-hydroxy imidazopropionyl-exendin-4 (HY-exendin-4) which is generated by substituting exendin-4 by hydroxyl group or carboxyl group; a beta-carboxyimidazopropionyl-exendin-4 (CX-exendin-4); a dimethylhistidyl-exendin-4 (DM-exendin-4) which is generated by modifying exendin-4 with two methyl groups; or an imidazoacetyl-exendin-4 (CA-exendin-4) which is generated by deleting the alpha-carbon of the N-terminal histidine residue.

GLP-1 is a hormone secreted by small intestine and normally functions to stimulate the biosynthesis and secretion of insulin, suppresses the glucagon secretion, and promotes glucose absorption into the cell. A glucagon precursor in small intestine is degraded into three peptides, which are glucagon, GLP-1, and GLP-2. Here, GLP-1 refers to GLP-1(1-37) which does not have a function to secret insulin, but when it is processed to the form of GLP-1(7-37), it becomes active. The amino acid sequence of GLP-1(7-37) is as follows:

```
GLP-1(7-37):
                                          (SEQ ID No. 3)
HAEGT FTSDV SSYLE GQAAK EFIAW LVKGR G
```

As used herein, "GLP-1 derivative" refers to a peptide which has at least 80% sequence homology to native GLP-1 and may be in a chemically modified form, while demonstrating at least the same or improved insulin secretion activity. As used herein, "GLP-1 fragment" refers to a form of peptide where one or more amino acids are added or deleted at the N-terminal or C-terminal of native GLP-1, wherein the added amino acid may be non-naturally occurring amino acids (e.g., D-type amino acid). As used herein, the term, long-acting insulinotropic peptide conjugate, refers to the peptide having enhanced durability of effects compared to native insulinotropic peptide. The long-acting insulinotropic peptide conjugate may be in form where an amino acid of native insulinotropic peptide is modified, substituted, added, or deleted; a form of conjugate where insulin is linked to a biodegradable polymer such as PEG; a form of conjugate where insulin is linked to a protein having high durability such as an albumin, immunoglobulin, and a fragment thereof; a form of conjugate where insulinotropic peptide is linked to a fatty acid which has a binding affinity with albumin in the body; or a form of insulinotropic peptide which is enclosed in a biodegradable nano-particles, but the type of long-acting insulinotropic peptide conjugate is not limited to the present invention.

As used herein, "GLP-1 variant" refers to a peptide having one or more amino acid sequences different from native GLP-1 and possessing the function of secreting insulin.

Exendin-3 and exendin-4 are the insulinotropic peptide consisted of 39 amino acids, having 53% amino acid sequence homology with GLP-1. The amino acid sequences of exendin-3 and exendin-4 are as follows:

```
Exendin-3:
                                          (SEQ ID No. 4)
HSDGT FTSDL SKQME EEAVR LFIEW LKNGG PSSGA PPPS Exendin-4:
                                          (SEQ ID No. 5)
HGEGT FTSDL SKQME EEAVR LFIEW LKNGG PSSGA PPPS
```

Exendin agonist refers to a substance having the same bioactivity as exendin by binding to the in vivo receptor of exendin, regardless of its structural similarity with exendin. An exendin derivative refers to a peptide which shows at least 80% sequence homology to native exendin and it may have some groups of amino acid residues chemically substituted (e.g., alpha-methylation, and alpha-hydroxylation), deleted (e.g., deamination), or modified (e.g., N-methylation), and such exendin derivative has a function of secreting insulin.

Exendin fragment refers to a form of peptide where one or more amino acids are added or deleted at the N-terminal or C-terminal of native exendin, wherein non-naturally occurring amino acids (e.g., D-type amino acid) may be added and such exendin fragment has a function of secreting insulin.

Exendin variant is a peptide that has one or more amino acid sequences different from native exendin and has a function of secreting insulin. The exendin variant comprises a peptide generated by substituting the 12th amino acid of exendin-4, lysine, by serine or arginine. A method for preparing each of exendin agonist, derivative, fragment, and variant can be used individually or in combination. For example, the scope of insulinotropic peptide comprises the insulinotropic peptide having one or more amino acid sequences different from native peptide and the N-terminal amino acid residue deaminated. The native insulinotropic peptide and modified insulinotropic peptide used in the present invention may be synthesized by a solid phase synthesis. Also, most of native peptide including native insulinotropic peptide can be produced by recombination method.

The long-acting insulinotropic peptide conjugate used in the present invention has a form of insulinotropic peptide linked to immunoglobulin fragment such as immunoglobulin Fc through a non-peptidyl linker or a peptidyl linker by using genetic recombination technique. The non-peptidyl linker is the same as described above. The long-acting insulinotropic peptide conjugate is prepared by using immunoglobulin fragment as in the long-acting insulin conjugate. The long-acting insulinotropic peptide conjugate maintains the physiological activity of existing insulinotropic peptide, such as promoting insulin synthesis and secretion, suppressing appetite, inducing weight loss, increasing the beta-cell sensitivity towards glucose in serum, promoting beta cell proliferation, delaying gastric emptying, and suppressing glucagon, and it also has enhanced in vivo durability of effects due to the increased serum half-life of insulinotropic peptide. Thus, the long-acting insulinotropic peptide conjugate is effective in the treatment of diabetes and obesity.

For preparation of long-acting insulinotropic peptide conjugate used in the present invention, one can refer to the following references: Korean Patent Registration No. 10-0725315, Korean Patent Publication No. 10-2009-0008151, and Korean Patent Registration No. 10-1058290. Those skilled in the art can prepare the long-acting insulinotropic peptide conjugate used in the present invention according to the above references.

Furthermore, the present inventors have previously developed a method for preparing a long-acting exendin-4 conjugate by first attaching PEG to lysine (Lys) residue of imidazo-acetyl exendin-4 (CA exendin-4), and linking the PEG-modified exendin-4 to an immunoglobulin Fc.

The insulin and insulinotropic peptide used in the present invent ion are linked with a carrier through a non-peptidyl polymer as a linker. The carrier that can be used in the present invention can be selected from the group consisting of immunoglobulin Fc region, albumin, transferrin, and PEG, and is preferably immunoglobulin Fc region.

Each of the long-acting insulin conjugate and long-acting insulinotropic peptide conjugate of the present invention has insulin or insulinotropic peptide linked to immunoglobulin Fc region through non-peptidyl linker, having durability and stability. In the present invention, the immunoglobulin Fc can be interchangeably used with immunoglobulin fragment.

In addition, since immunoglobulin Fc region has a relatively low molecular weight compared to the whole immunoglobulin molecule, a use thereof can be beneficial for preparing and purifying the conjugate as well as for getting high yield. Furthermore, the immunoglobulin Fc region does not contain a Fab fragment, which is highly heterogeneous due to different amino acid sequences according to the antibody subclasses, and thus it can be expected that the immunoglobulin Fc region has an increased homogeneity and is less antigenic.

As used herein, "immunoglobulin Fc region" refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, it may be a fragment having a deletion in a relatively long portion of the amino acid sequence of CH2 and/or CH3. That is, the immunoglobulin Fc region of the present invention may comprise (1) a CH1 domain, a CH2 domain, a CH3 domain and a CH4 domain, (2) a CH1 domain and a CH2 domain, (3) a CH1 domain and a CH3 domain, (4) a CH2 domain and a CH3 domain, (5) a combination of one or more domains and an immunoglobulin hinge region (or a portion of the hinge region), and (6) a dimer of each domain of the heavy-chain constant regions and the light-chain constant region.

Further, the immunoglobulin Fc region of the present invention includes a native amino acid sequence and a sequence derivative (mutant) thereof. An amino acid sequence derivative has a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification.

In addition, other various derivatives are possible, including derivatives having a deletion of a region capable of forming a disulfide bond, a deletion of several amino acid residues at the N-terminus of a native Fc form, or an addition of methionine residue to the N-terminus of a native Fc form. Furthermore, to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in WO 97/34631 and WO 96/32478.

Amino acid exchanges in proteins and peptides, which do not generally alter the activity of molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly, in both directions. The Fc region, if desired, may be modified by phosphorylation, sulfation, acrylation, glycosylation, methylation, farnesylation, acetylation, amidation, and the like.

The aforementioned Fc derivatives are derivatives that have a biological activity identical to that of the Fc region of the present invention or improved structural stability, for example, against heat, pH, or the like.

In addition, these Fc regions may be obtained from native forms isolated from humans and other animals including cows, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size-exclusion chromatography to isolate Fc or pF'c. Preferably, a human-derived Fc region is a recombinant immunoglobulin Fc region that is obtained from a microorganism.

In addition, the immunoglobulin Fc region of the present invention may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in-vivo. In this regard, an immunoglobulin Fc region in a deglycosylated or aglycosylated form may be more suitable to the object of the present invention as a drug carrier.

The term "deglycosylation", as used herein, means to enzymatically remove sugar moieties from an Fc region, and the term "aglycosylation" means that an Fc region is produced in an unglycosylated form by a prokaryote, preferably E. coli.

Meanwhile, the immunoglobulin Fc region may be derived from human or animals such as cows, goats, pigs, mouse, rabbits, hamsters, rats, guinea pigs, and preferably human.

In addition, the immunoglobulin Fc region may be an Fc region that is derived from IgG, IgA, IgD, IgE and IgM, or that is made by combination or hybrid thereof. Preferably, it is derived from IgG or IgM, which is among the most abundant proteins in the human blood, and most preferably from IgG, which is known to enhance the half-life of ligand-binding proteins.

The term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

The term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3 and CH4 of IgG Fc, IgM Fc, IgA Fc, IgE Fc and IgD Fc, and may include the hinge region.

On the other hand, IgG is divided into IgG1, IgG2, IgG3 and IgG4 subclasses, and the present invention includes combinations or hybrids thereof. Preferred are IgG2 and IgG4 subclasses, and most preferred is the Fc region of IgG4 rarely having effector functions such as complement dependent cytotoxicity (CDC).

As the drug carrier of the present invention, the most preferable immunoglobulin Fc region is a human IgG4-derived non-glycosylated Fc region. The human-derived Fc region is more preferable than a non-human derived Fc region, which may act as an antigen in the human body and cause undesirable immune responses such as the production of a new antibody against the antigen.

The liquid formulation of a combination of long-acting insulin conjugate and long-acting insulinotropic peptide conjugate of the present invention comprises a therapeutically effective amount of long-acting insulin conjugate and long-acting insulinotropic peptide conjugate. The concentration of long-acting insulin conjugate used in the present invention is 0.1 mg/ml to 200 mg/ml, and preferably 10 mg/ml to 200 mg/ml. The concentration of long-acting insulinotropic peptide conjugate used in the present invention is 0.1 mg/ml to 200 mg/ml, and preferably 0.5 mg/ml to 150 mg/ml. The liquid formulation of long-acting insulin conjugate and insulinotropic peptide conjugate of the present invention at high concentration comprises insulin conjugate and insulinotropic peptide conjugate at high concentration per dose, compared to the existing liquid formulation at low concentration. Thus, it can stably provide insulin into the body, allowing co-administration of the insulin conjugate and insulinotropic peptide conjugate at high concentration and stably store them without precipitation, unlike the existing liquid formulation.

As used herein, the term "stabilizer" refers to a substance that allows stable storing of the long-acting insulin conjugate and long-acting insulinotropic peptide. The term "stabilization" refers to that the loss of an active ingredient is less than a certain amount, typically less than 10% during certain period and under specific storage condition. A formulation is regarded as stable formulation when the residual purity of long-acting insulin conjugate and long-acting insulinotropic peptide therein is 90% or more, and more preferably 92 to 95% after being stored at 5±3° C. for 2 years, at 25±2° C. for 6 months, or at 40±2° C. for 1 to 2 weeks. As for the proteins like long-acting insulin conjugate or long0acting insulinotropic peptide, the storage stability is important for providing an accurate dosage as well as for suppressing the potential formation of antigenic substances against the long-acting insulin conjugate and long-acting insulinotropic peptide. During storage, 10% loss of long-acting insulin conjugate or long-acting insulinotropic peptide is acceptable for a substantial administration unless it causes the formation of aggregates or fragments in the composition leading to the formation of antigenic compounds.

The stabilizer of the present invention preferably comprises a buffer, a sugar alcohol, a sodium chloride as isotonic agent, and a non-ionic surfactant for stabilizing a combination of the long-acting insulin conjugate and long-acting insulinotropic peptide conjugate, and may further comprise methionine.

The buffer works to maintain the pH of solution to prevent a sharp pH change in the liquid formulation for stabilizing a combination of long-acting insulin conjugate and long-acting insulinotropic peptide conjugate. The buffer may include an alkaline salt (sodium or potassium phosphate or hydrogen or dihydrogen salts thereof), sodium citrate/citric acid, sodium acetate/acetic acid, and any other pharmaceutically acceptable pH buffer known in the art, and a combination thereof. The preferred example of such buffer includes a citrate buffer, acetate buffer, and phosphate buffer. Among them, a sodium acetate buffer or sodium citrate buffer is preferred. The concentration of acetic acid constituting a sodium acetate buffer is preferably 5 mM to 100 mM, and more preferably 5 mM to 50 mM of a total volume of the solution. The pH of buffer is preferably 4.0 to 8.0, more preferably 5.0 to 7.0, and even more preferably 5.0 to 6.5.

Sugar alcohol acts to increase the stability of a combination of the long-acting insulin conjugate and long-acting insulinotropic peptide conjugate. In the present invention, the concentration of sugar alcohol is preferably 1 to 20% (w/v) of a total volume of formulation, and more preferably 1 to 15% (w/v) of a total volume of formulation. Examples of the sugar alcohol useful in the present invention include mannitol, and sorbitol, and preferred example is mannitol.

Isotonic agent has the effect of maintaining the proper osmotic pressure when a combination of the long-acting insulin conjugate and long-acting insulinotropic peptide conjugate in solution is being injected into the body. Also, isotonic agent has an effect of further stabilizing the combination in solution. Isotonic agent is typically a water-soluble inorganic salt, including sodium chloride, sodium sulfate, sodium citrate and preferably sodium chloride. The content of isotonic agent may be adjusted appropriately according to the type and amount of components included in the formulation so that a liquid formulation comprising all the mixture can be an isotonic solution. The concentration of such isotonic agent may be 0.5 mg/ml to 30 mg/ml of a total volume of the solution, but is not limited thereto.

The non-ionic surfactant reduces the surface tension of the protein solution to prevent the absorption or aggregation of proteins onto a hydrophobic surface. Examples of the non-ionic surfactant useful in the present invention include polysorbates, poloxamers and combinations thereof, with preference for polysorbates. Among the non-ionic surfactants of polysorbates are polysorbate 20, polysorbate 40, polysorbate 60, and polysorbate 80. The most preferred non-ionic surfactant is polysorbate 20.

It is inappropriate to use a non-ionic surfactant at high concentration in liquid formulation, and this is due to the fact that non-ionic surfactant at high concentration induces interference effects when measuring protein concentration and determining protein stability through analytic methods such as UV-spectroscopy or isoelectric focusing, thereby causing difficulty in examining the protein stability accurately. Therefore, the liquid formulation of the present invention comprises the non-ionic surfactant preferably at a low concentration less than 0.2% (w/v), more preferably at 0.001% to 0.05% (w/v).

A methionine comprised in the stabilizer of the present invention has an effect of further stabilizing a target protein by suppressing the formation of impurities, which may occur due to oxidation of the protein in solution. The concentration of methionine is 0.005% to 0.1% (w/v) of a total volume of the solution, and preferably 0.01% to 0.1% (w/v) of a total volume of the solution.

According to one example of the present invention, it was demonstrated that when sodium chloride was added as isotonic agent in the presence of buffer, sugar alcohol, and non-ionic surfactant, the storage stability of a combination of long-acting insulin conjugate and long-acting insulinotropic peptide conjugate was significantly increased. This indicates that use of sodium chloride as isotonic agent simultaneously with buffer, sugar alcohol, and non-ionic surfactant induces synergic effects, thereby providing high stability to a combination of the long-acting insulin conjugate and long-acting insulinotropic peptide conjugate.

It is preferred that the stabilizer of the present invention does not contain albumin. Since the human serum albumin available as a stabilizer of protein is produced from human serum, there is always the possibility that it may be contaminated with pathogenic viruses of human origin. Gelatin or bovine serum albumin may cause diseases or may be apt to induce an allergic response in some patients. Free of heterologous proteins such as serum albumins of human or animal origin or purified gelatin, the stabilizer of the present invention has no possibility of causing viral contamination.

In addition, the stabilizer of the present invention may further comprise sugars, polyalcohol, or neutral amino acids. Preferable examples of sugars, which may be further added to increase the storage stability of a combination of the long-acting insulin conjugate and long-acting insulinotropic peptide conjugate, include monosaccharides such as mannose, glucose, fucose and xylose, and polysaccharides such as lactose, maltose, sucrose, raffinose and dextran. Preferred examples of polyalcohol include propylene glycol, low-molecular weight polyethylene glycol, glycerol, low-molecular weight polypropylene glycol, and a combination thereof.

The liquid formulation of the present invention may further comprise other substances and materials known in the art selectively in addition to the above-described buffer, isotonic agent, sugar alcohol, and non-ionic surfactant, as long as the effect of the present invention is not affected.

The albumin-free liquid formulation of the combination at high concentration of the present invention, which provides stability to a combination of the long-acting insulin conjugate and insulinotropic peptide conjugate does not have a risk of viral contamination, while providing an excellent storage stability with a simple formulation, and thus the present formulation can be provided more cost-effectively compared to other stabilizer or free-dried formulation.

Also, since the liquid formulation of the present invention comprises the long-acting insulin conjugate and insulinotropic peptide conjugate which have an enhanced duration of physiological activity compared to a native peptide, it can be used as an effective drug formulation by retaining the protein activity in the body for a longer period compared to the conventional insulin and insulinotropic peptide formulation. Also, the present liquid formulation provides an excellent stability for storing a combination of long-acting insulin conjugate and insulinotropic peptide conjugate at high concentration.

Preferably, the liquid formulation of the present invention may comprise long-acting insulin conjugate, in which insulin and insulinotropic peptide are linked to an immunoglobulin fragment through polyethylene glycol; long-acting insulinotropic peptide; and an albumin-free stabilizer, wherein the stabilizer comprises acetate buffer, mannitol, polysorbate 20, and sodium chloride. Also, the liquid formulation may further comprise methionine.

As another aspect, the present invention provides a method for preparing the liquid formulation of the present invention.

A stable liquid formulation of a combination of long-acting insulin conjugate and insulinotropic peptide conjugate can be prepared through generating a long-acting insulin and insulinotropic peptide conjugate, and mixing the generated long-acting insulin and insulinotropic conjugate with a stabilizer comprising a buffer, sugar alcohol, non-ionic surfactant, and isotonic agent.

As another aspect, the present invention provides a composition for preventing or treating diabetes, comprising the insulin conjugate and insulinotropic peptide conjugate.

The composition of the present invention is characterized in that it allows co-administration of the long-acting insulin conjugate and long-acting insulinotropic peptide conjugate.

When the long-acting insulin conjugate and long-acting insulinotropic peptide conjugate are co-administered, the long-acting insulin conjugate acts on an insulin receptor, and the long-acting insulinotropic peptide conjugate acts on a glucagon-like peptide-1 receptor simultaneously. Thus, the co-administration of the two conjugates can reduce the blood glucose level more effectively demonstrating stable changes, compared to the separate administrations of the two conjugates. Furthermore, when the conjugates are co-administered, it reduces the risk of hypoglycemia, which can be shown in the administration of insulin alone, reduces the body weight, and also reduces the total dosage of insulin by comprising insulinotropic peptide. In addition, a dosage of insulinotropic peptide such as exendin-4 can be reduced, and thus the co-administration has the advantages of reducing side effects such as nausea and vomiting which can be seen when exendin-4 is administered alone. Use of long-acting insulin conjugate and long-acting insulinotropic peptide conjugate can increase the half-life and in vivo durability of drug significantly, and thus it is highly beneficial for treating diabetes by reducing the frequency of administration for a chronic patient who needed the administration everyday, thereby improving the patient's life quality. In addition, the pharmaceutical composition of the present invention has excellent in vivo durability and titer, and use thereof can significantly reduce the dosage by employing a co-administration method.

The long-acting insulin conjugate and long-acting insulinotropic peptide conjugate can be administered simultaneously, successively, or in reverse order. Also, they can be administered simultaneously as a combination of the two in an effective amount. Preferably, the long-acting insulin conjugate and long-acting insulinotropic peptide conjugate can be put in a single container and then co-administered.

Furthermore, the composition for co-administration of long-acting insulin conjugate and long-acting insulinotropic peptide conjugate of the present invention may be in a form of kit for diabetes treatment prepared in a single container. Such kit may include a pharmaceutically acceptable carrier and an instruction manual for using the kit.

Streptozotocin (STZ)-induced hyperglycemic mouse was co-administered with the long-acting insulin conjugate and long-acting insulinotropic peptide conjugate, and the changes in blood glucose level were monitored. As a result, when the conjugates were co-administered, the blood glucose level changes were more stable than when the conjugates were administered separately. In another experiment, type 2 diabetes model mouse was co-administered with the long-acting insulin conjugate and long-acting insulinotropic peptide conjugate once a week, and then the difference in fasting blood glucose level before and after administration was compared. As a result, the co-administration showed higher effect in regulating blood glucose level, compared to the separate administrations of the two conjugates, and the weight gain after insulin administration was not observed, thereby confirming that the co-administration can reduce the side effects of weight gain due to insulin.

As used herein, "diabetes" refers to a metabolic disease where secretion of insulin is lacking or insulin cannot function properly. By co-administering the composition of the present invention to a subject, diabetes may be treated by regulating blood glucose level.

As used herein, the term "prevention" refers to all actions that prevent or delay the onset of diabetes by co-administering the composition of the present invention. The term "treatment" refers to all actions that can alleviate or beneficially change the symptoms of diabetes by co-administering the composition of the present invention. The diabetes treatment can be applied to any mammals which may develop diabetes, and examples of such mammals include human and primates, as well livestock such as cows, pigs, sheep, horses, dogs, and cats without limitation, and preferably human.

As used herein, the term "administration" refers to the introduction of predetermined amount of a substance into the patient by a certain suitable method. The compositions may be administered via any of the conventional routes, as long as it is able to reach a target tissue. The routes for administration include intraperitoneal, intravenous, intramuscular, subcutaneous, intradermal, oral, topical, intranasal, intrapulmonary and intrarectal administration, but are not limited thereto. However, since peptides are digested upon oral administration, active ingredients of a composition for oral administration need to be coated or formulated for protection against degradation in the stomach. Preferably, the conjugate may be administered in an injectable form. In addition, the compositions may be administered using a certain apparatus capable of transporting the active ingredients into a target cell.

In addition, the pharmaceutical composition of the present invention can be determined by several factors including the types of diseases to be treated, administration routes, the age, gender, and weight of patient, and severity of disease, as well as the types of active component in drug.

Furthermore, the pharmaceutical composition of the present invention may comprise pharmaceutically acceptable carriers. As used herein, "pharmaceutically acceptable carrier" refers to a carrier or diluent that does not interrupt the physiological activity and properties of the administered compound without stimulating a subject. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable formulation, the pharmaceutically acceptable carrier may include a buffering agent, a preserving agent, an analgesic, a solubilizer, an isotonic agent, and a stabilizer. For formulations of topical administration, the pharmaceutically acceptable carrier may include a base, an excipient, a lubricant, and a preservative. The pharmaceutical composition of the present invention may be formulated in various forms by adding the pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into single-dose ampule or multidose container. The pharmaceutical composition may be also formulated into solutions, suspensions, tablets, pills, capsules and sustained release formulation.

As another aspect, the present invention provides a method for preventing or treating diabetes, comprising administering the composition comprising the long-acting insulin conjugate and long-acting insulinotropic peptide conjugate to a subject who may develop diabetes or already has diabetes.

In the administration step, the long-acting insulin conjugate and long-acting insulinotropic peptide conjugate may be co-administered, wherein a suitable effective amount of the conjugates are combined and administered concurrently.

The composition of the present invention comprising both of the long-acting insulin conjugate and long-acting insulinotropic peptide conjugate can effectively reduce the blood glucose level even with reduction of administration frequency, and does not cause side effect such as weight gain, and thus it can be effectively used for preventing or treating diabetes.

Mode for Invention

Hereinafter, the present invention will be described in more detail with reference to Examples. However, these Examples are for illustrative purposes only, and the invention is not intended to be limited by these Examples.

Example 1: Evaluation of Stability of Long-Acting Insulin Conjugate

The long-acting insulin conjugate was developed as a strategy for increasing the serum half-life of drug and preventing hypoglycemia in the body. Thus, the insulin conjugate, which is generated by site-specific conjugation of an immunoglobulin Fc region, non-peptidyl polymer, and insulin through covalent bond, has remarkably increased serum half-life and reduces the risk of hypoglycemia.

In order to evaluate the stability of such long-acting insulin conjugate, the formulations were prepared in the compositions of Table 1 and stored at 40° C. for 2 weeks, and the stability of peptide therein was analyzed by ion exchange chromatography (IE-HPLC).

At this time, the main factors contributing to the stability of peptide were set to be a pH, type and concentration of buffer, type of isotonic agent, concentration of sugar alcohol consisting of mannitol, type of surfactant, concentration of surfactant consisting of polysorbate 20, the presence or absence of other additives, and co-addition of methionine and sodium chloride. The concentration of long-acting insulin conjugate in each composition was 61.1 mg/ml, and these formulations were used for the experiment.

IE-HPLC (%) of Table 1 represents a value of Area %/Start Area %, demonstrating the residual purity of long-acting insulin conjugate, compared to the initial purity.

TABLE 1

| | Main Factors | IE-HPLC(%) |
|---|---|---|
| pH | 5.0~5.4 | Protein precipitation |
| | 5.6 | 87.9 |
| | 6.0 | 88.1 |
| | 6.5 | 81.9 |
| | 7.0 | 70.4 |

TABLE 1-continued

| | Main Factors | IE-HPLC(%) |
|---|---|---|
| Type of buffer | Sodium acetate | 91.5 |
| | Sodium citrate | 90.5 |
| | Sodium phosphate | 89.4 |
| | Histidine | Protein precipitation |
| Concentration of buffer | 5 mM sodium acetate | 83.2 |
| | 10 mM sodium acetate | 83.6 |
| | 20 mM sodium acetate | 83.5 |
| | 40 mM sodium acetate | 83.4 |
| Type of isotonic agent | Sodium chlrodie | 83.5 |
| | Glycerin | 81.7 |
| | Sorbitol | 81.6 |
| Concentration of mannitol | 2.5% | 74.4 |
| | 5.0% | 76.1 |
| | 10.0% | 76.8 |
| Type of surfactant | Polysorbate 20 | 83.5 |
| | Polysorbate 80 | 83.3 |
| | Poloxamer 188 | 83.0 |
| Concentration of polysorbate 20 | 0.005% | 88.4 |
| | 0.01% | 88.5 |
| | 0.02% | 88.9 |
| Presence of additive | w/o zinc chloride | 77.9 |
| | w/20 μg/ml zinc chloride | 70.9 |
| | w/o phenol | 74.4 |
| | w/1.5 mg/ml phenol | 73.5 |
| | w/o methionine | 74.4 |
| | w/0.1 mg/ml methionine | 77.0 |

TABLE 2

| | pH | Buffer | Isotonic agent | Sugar alcohol | Surfactant |
|---|---|---|---|---|---|
| #1 | 5.6 | 10 mM Sodium acetate | 10 mg/ml NaCl | 10% Mannitol | 0.02% Polysorbate 20 |
| #2 | 6.0 | 10 mM Sodium acetate | 10 mg/ml NaCl | 10% Mannitol | 0.02% Polysorbate 20 |

As shown in Table 2, the long-acting insulin conjugate was most stable in the liquid formulation comprising a buffer consisting of sodium acetate, an isotonic agent consisting of sodium chloride, a sugar alcohol consisting of mannitol, and a surfactant consisting of polysorbate 20, at a pH of 5.6 or 6.0.

Example 2: Evaluation of Stability of Long-Acting Insulinotropic Peptide Conjugate In order to confirm the solubility of long-acting insulinotropic peptide conjugate at various pH and depending on the presence of stabilizer, different liquid formulations of long-acting insulinotropic peptide conjugate were prepared in the following compositions shown in Table 3 and stored at 40° C. for 1 week. Then the stability of the conjugate was compared by monitoring the protein precipitation by naked eyes. In each composition, the concentration of the long-acting insulinotropic peptide conjugate was 10 mg/ml, and experiment was performed using these formulations.

TABLE 3

|  | pH | Buffer | Isotonic agent | Sugar alcohol | Surfactant |
|---|---|---|---|---|---|
| #1 | 5.0 | 10 mM Sodium acetate | 10 mg/ml NaCl | 10% Mannitol | 0.02% Polysorbate 20 |
| #2 | 5.2 | 10 mM Sodium acetate | 10 mg/ml NaCl | 10% Mannitol | 0.02% Polysorbate 20 |
| #3 | 5.4 | 10 mM Sodium acetate | 10 mg/ml NaCl | 10% Mannitol | 0.02% Polysorbate 20 |
| #4 | 5.6 | 10 mM Sodium acetate | 10 mg/ml NaCl | 10% Mannitol | 0.02% Polysorbate 20 |
| #5 | 5.6 | 10 mM Sodium acetate | 10 mg/ml NaCl | 5% Mannitol | 0.02% Polysorbate 20 |
| #6 | 5.6 | 10 mM Sodium acetate | — | 10% Mannitol | 0.02% Polysorbate 20 |

Figure 1:
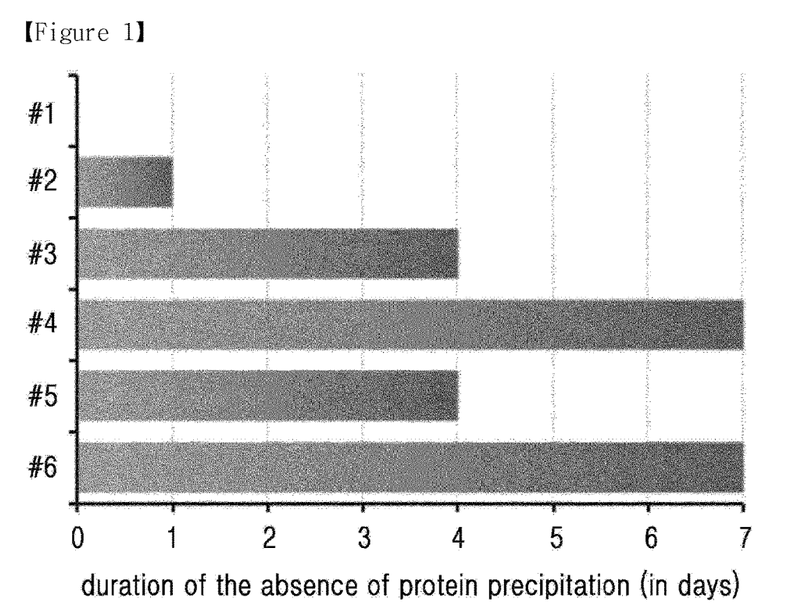
FIG. 1 shows the monitoring results on the generation of precipitation for the formulations of long-acting insulinotropic peptide conjugate prepared in the compositions of Table 3 at 40° C. for 1 week.

The duration (in days) of the absence of protein precipitation in FIG. 1 represents the time during which a protein precipitation did not occur after storing the formulation at 40° C. As shown above, with sodium acetate, pH 5.0 to 5.4 (#1, #2, and #3), or with 5% (w/v) mannitol (#5), the protein precipitation occurred at 40° C. within 4 days of storage. However, when the pH was 5.6 and 10% (w/v) mannitol was added in the formulation, the solubility was increased, and the precipitation did not occur for 7 days (FIG. 1).

Example 3: Evaluation of the Stability of a Combination of Long-Acting Insulin Conjugate and Long-Acting Insulinotropic Peptide Conjugate Based on individual liquid formulation, the stability of a combination of long-acting insulin conjugate and long-acting insulinotropic peptide conjugate was compared. Also, it was determined how the addition of sodium chloride and methionine, which are important for stabilizing the long-acting insulin conjugate and long-acting insulinotropic peptide conjugate respectively, affects the stability of a combination of long-acting insulin conjugate and long-acting insulinotropic peptide conjugate.

The liquid formulations of long-acting insulin conjugate, long-acting insulinotropic peptide conjugate, or a combination of the two were prepared in the following compositions shown in Table 4 and stored at 40° C. for 4 weeks. Then the stability test was performed on the formulation of the combination of two conjugates compared to that of individual conjugate through monitoring the protein precipitation and through using ion exchange chromatography (IE-HPLC), size exclusion chromatography (SE-HPLC), and reverse phase-high performance liquid chromatography (RP-HPLC).

The concentration of long-acting insulinotropic peptide conjugate (control-1, #1 to #4) and long-acting insulin conjugate (control-2, #1 to #4) in each liquid formulation was 10 mg/ml and 61.1 mg/ml respectively.

TABLE 4

|  | Buffer | Isotonic agent | Sugar alcohol | Surfactant | Others |
|---|---|---|---|---|---|
| Control-1 (long-acting insulinotropic peptide conjugate itself) | 20 mM Sodium citrate (pH 5.6) | — | 10% Mannitol | 0.005% Polysorbate 20 | 0.01% Methionine |
| Control-2 (long-acting insulin conjugate itself) | 10 mM Sodium acetate (pH 6.0) | 10 mg/ml NaCl | 10% Mannitol | 0.02% Polysorbate 20 | — |
| #1 | 20 mM Sodium citrate (pH 5.6) | — | 10% Mannitol | 0.005% Polysorbate 20 | 0.01% Methionine |
| #2 | 20 mM Sodium citrate (pH 5.6) | 10 mg/ml NaCl | 10% Mannitol | 0.005% Polysorbate 20 | 0.01% Methionine |
| #3 | 10 mM Sodium acetate (pH 6.0) | 10 mg/ml NaCl | 10% Mannitol | 0.02% Polysorbate 20 | — |
| #4 | 10 mM Sodium acetate (pH 6.0) | 10 mg/ml NaCl | 10% Mannitol | 0.02% Polysorbate 20 | 0.01% Methionine |

Figure 2A:
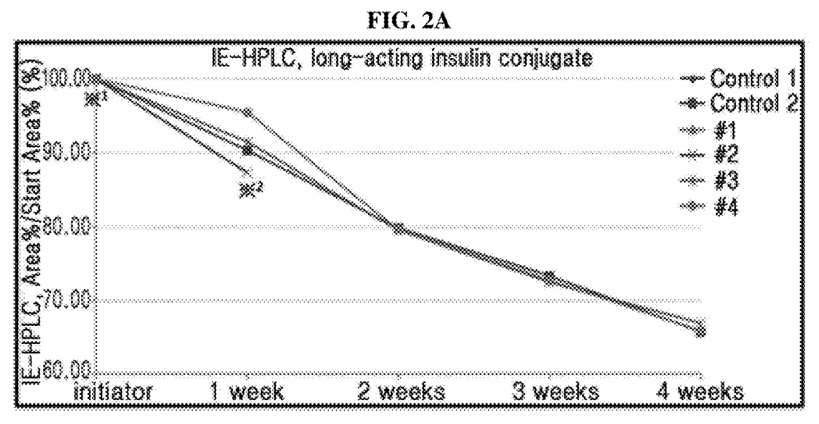
FIG. 2A and FIG. 2B show the results of IE-HPLC analysis and RP-HPLC, respectively, on the long-acting insulin conjugate and insulinotropic peptide conjugate which were prepared in the compositions of Table 4 and stored at 40° C. for 4 weeks.
Figure 2B:
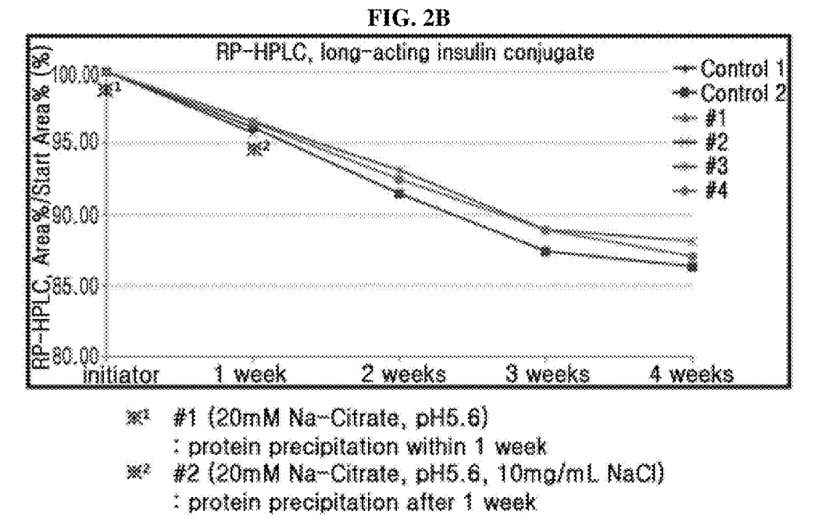

In FIGS. 2A, 2B, 3A, and 3B, the IE-HPLC and RP-HPLC analysis showed the value of area %/start area %, representing the residual purity of the long-acting insulin conjugate and long-acting insulinotropic peptide conjugate compared to the initial purity. Among them, FIG. 2A and FIG. 2B show the results of IE-HPLC and RP-HPLC analysis, respectively, for long-acting insulin conjugate, while FIG. 3 demonstrates the results of IE-HPLC and RP-HPLC analysis for long-acting insulinotropic peptide conjugate.

As shown above, when the stability of a combination of long-acting insulin conjugate and long-acting insulinotropic peptide conjugate is compared with that of long-acting insulin conjugate or long-acting insulinotropic peptide conjugate, it was found that the long-acting insulin conjugate had similar purity and stability in combined formulations (formulations #3 and #4) and in separate formulations (FIGS. 2A and 2B).

Figure 3A:
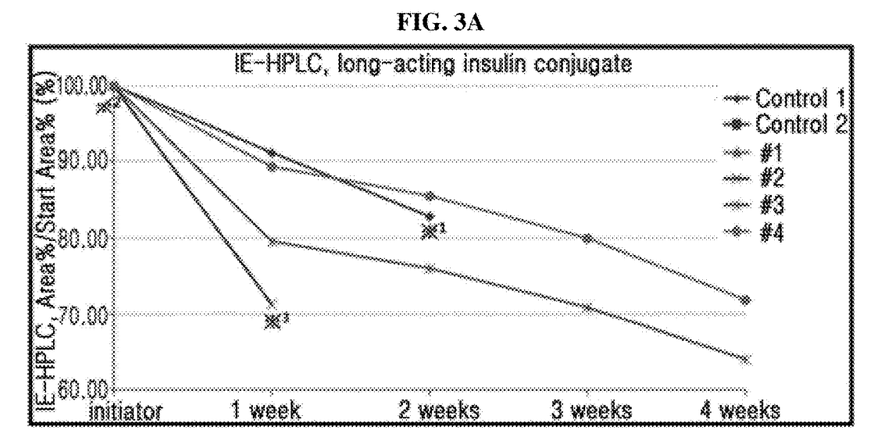
FIG. 3A and FIG. 3B show the results of IE-HPLC analysis and RP-HPLC, respectively, on the long-acting insulin conjugate and insulinotropic peptide conjugate which were prepared in the compositions of Table 4 and stored at 40° C. for 4 weeks.
Figure 3B:
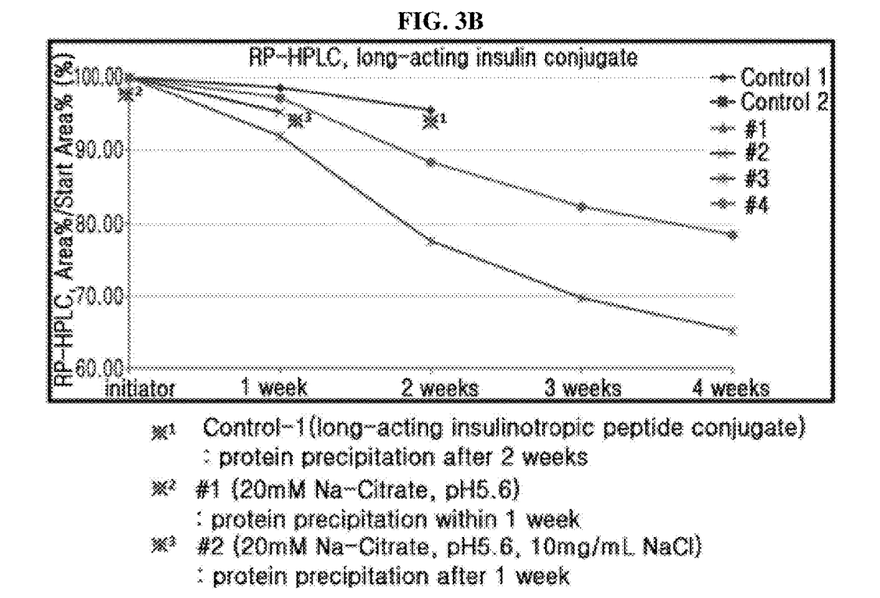

However, when 0.01% (w/v) methionine was included in the liquid formulation comprising 10 mM sodium acetate, pH 6.0, 10 mg/ml sodium chloride, 10% (w/v) mannitol, and 0.02% (w/v) polysorbate 20 (i.e., formulation #4), the stability of long-acting insulinotropic peptide conjugate was improved compared to when it was in the formulation lacking methionine (FIGS. 3A and 3B). This might be due to the fact that methionine acts to prevent the oxidation of long-acting insulinotropic peptide conjugate. The comparison with the separate formulation of long-acting insulinotropic peptide conjugate could not be performed due to excessive amount of precipitation.

Figure 4:
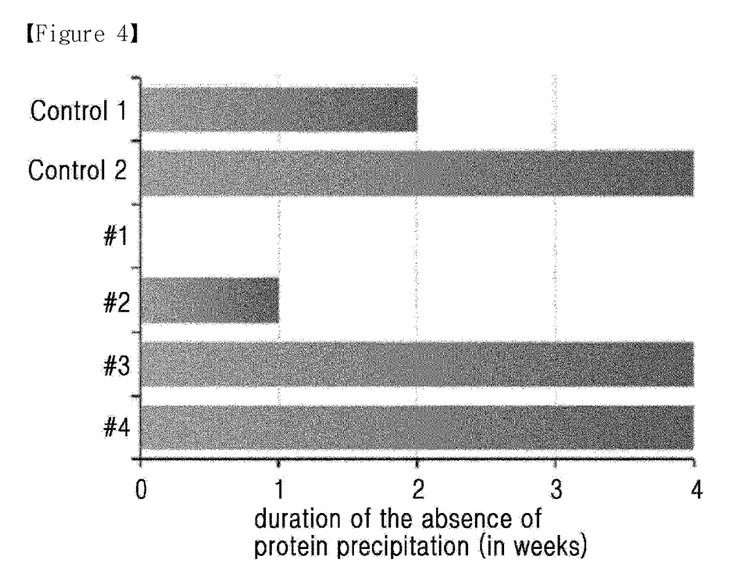
FIG. 4 shows the monitoring results on the generation of protein precipitation in each of the combined formulations having different compositions, compared to a separate formulation.

As shown in FIG. 4, the separate formulation of long-acting insulinotropic peptide conjugate had protein precipitation within 2 weeks, whereas the formulation of a combination of long-acting insulin conjugate and long-acting insulinotropic peptide conjugate (formulations #3 and #4) had increased solubility and the precipitation therein was suppressed for relatively longer period up to 4 weeks.

These results support that the composition of the liquid formulation of the present invention can maintain high stability of a combination of insulinotropic peptide conjugate and insulin conjugate at high concentration.

Example 4: Evaluation of the Stability of a Combination of Long-Acting Insulin Conjugate and Long-Acting Insulinotropic Peptide Conjugate Depending on the Concentrations of Isotonic Agent and Sugar Alcohol The stability of a combination of long-acting insulin conjugate and long-acting insulinotropic peptide conjugate was compared between the combination of the conjugates in a liquid formulation comprising 4.8 to 6.7 mg/ml sodium chloride as isotonic agent, 1 to 2% (w/v) mannitol as sugar alcohol, and mannitol and the combination in the liquid formulation confirmed in Example 2 (10 mM sodium acetate, pH 6.0, 10 mg/ml sodium chloride, 10% (w/v) mannitol, 0.02% (w/v) polysorbate 20, 0.01% (w/v) methionine).

The liquid formulation of a combination of long-acting insulin conjugate and long-acting insulinotropic peptide conjugate was prepared in the following compositions shown in Table 5 and stored at 25° C. for 4 weeks. Then the stability of the conjugates was examined by IE-HPLC, SE-HPLC, and RP-HPLC.

IE-HPLC (%) and RP-HPLC (%) of Tables 6 and 7 represent the value of area %/start area %, demonstrating the residual purity of a combination of long-acting insulin conjugate and long-acting insulinotropic peptide conjugate, compared to the initial purity. Among them, Table 6 demonstrates the results of IE-HPLC and RP-HPLC analysis on the long-acting insulin conjugate while Table 7 shows the results of IE-HPLC and RP-HPLC analysis on the long-acting insulinotropic peptide conjugate.

TABLE 5

| | Buffer | Isotonic agent | Sugar alcohol | Surfactant | Others |
|---|---|---|---|---|---|
| Control | 10 mM Sodium acetate (pH 6.0) | 10 mg/ml NaCl | 10% Mannitol | 0.02% Polysorbate 20 | 0.01% Methionine |
| #1 | 10 mM Sodium acetate (pH 6.0) | 4.8 mg/ml NaCl | 1% Mannitol | 0.02% Polysorbate 20 | 0.01% Methionine |
| #2 | 10 mM Sodium acetate (pH 6.0) | 4.8 mg/ml NaCl | 2% Mannitol | 0.02% Polysorbate 20 | 0.01% Methionine |
| #3 | 10 mM Sodium acetate (pH 6.0) | 6.7 mg/ml NaCl | 1% Mannitol | 0.02% Polysorbate 20 | 0.01% Methionine |
| #4 | 10 mM Sodium acetate (pH 6.0) | 6.7 mg/ml NaCl | 2% Mannitol | 0.02% Polysorbate 20 | 0.01% Methionine |

TABLE 6

| | IE-HPLC (%) | | | | | RP-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 weeks |
| Control | 100 | 98.20 | 95.50 | 94.78 | 94.05 | 100 | 100 | 99.63 | 99.40 | 99.17 |
| #1 | 100 | 98.21 | 96.84 | 95.26 | 94.68 | 100 | 99.92 | 99.32 | 99.20 | 99.07 |
| #2 | 100 | 98.18 | 96.80 | 95.18 | 93.56 | 100 | 99.99 | 98.86 | 98.81 | 98.75 |
| #3 | 100 | 96.85 | 94.70 | 93.62 | 93.53 | 100 | 99.93 | 99.44 | 99.30 | 99.15 |
| #4 | 100 | 97.74 | 95.78 | 95.28 | 94.8 | 100 | 99.88 | 99.33 | 99.19 | 99.06 |

TABLE 7

| | IE-HPLC (%) | | | | | RP-HPLC (%) | | | | |
|---|---|---|---|---|---|---|---|---|---|---|
| | Start | 1 week | 2 weeks | 3 weeks | 4 weeks | Start | 1 week | 2 weeks | 3 weeks | 4 eeks |
| Control | 100 | 96.32 | 92.53 | 88.61 | 84.69 | 100 | 94.93 | 94.16 | 89.68 | 85.19 |
| #1 | 100 | 96.48 | 92.61 | 89.83 | 85.78 | 100 | 94.95 | 92.37 | 88.71 | 85.05 |
| #2 | 100 | 97.20 | 93.40 | 90.34 | 87.78 | 100 | 95.29 | 94.19 | 90.01 | 87.43 |
| #3 | 100 | 96.86. | 93.61 | 91.15 | 87.61 | 100 | 95.82 | 95.17 | 90.12 | 88.06 |
| #4 | 100 | 97.02 | 93.95 | 91.41 | 87.94 | 100 | 94.93 | 93.85 | 90.02 | 87.70 |

As shown above, when the concentration of sodium chloride was reduced to 4.8 mg/ml and the concentration of mannitol was reduced to 1 to 2% (w/v) (formulations #1 and #2) and when the concentration of sodium chloride was reduced to 6.7 mg/ml and the concentration of mannitol was reduced to 1 to 2% (w/v) (formulations #3 and #4) compared to the liquid formulation confirmed in Example 2 (10 mM sodium acetate, pH 6.0, 10 mg/ml sodium chloride, 10% (w/v) mannitol, 0.02% (w/v) polysorbate 20, 0.01% (w/v) methionine), all four tested formulations showed high stability as similar to the liquid formulation confirmed in Example 3.

These results support that if the composition of liquid formulation of the present invention comprises sodium chloride as isotonic agent and mannitol as sugar alcohol, even when the concentration of sodium chloride as isotonic agent and that of mannitol as sugar alcohol are low, it can provide the same extent of stability to a combination of the insulin conjugate and insulinotropic peptide conjugate.

Based on the above description, it will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A liquid formulation of a combination of a long-acting insulin conjugate and a long-acting insulinotropic peptide conjugate, comprising a pharmaceutically effective amount of the long-acting insulin conjugate, a pharmaceutically effective amount of the long-acting insulinotropic peptide conjugate and albumin-free stabilizer,
   wherein the stabilizer comprises a buffer, a sugar alcohol, a non-ionic surfactant, and an isotonic agent;
   wherein the long-acting insulin conjugate is in a form in which an insulin is linked to an immunoglobulin Fc region;
   wherein the long-acting insulinotropic peptide conjugate is in a form in which an insulinotropic peptide is linked to the immunoglobulin Fc region; and
   wherein a pH of the buffer ranges from 5.0 to 7.0.

2. The liquid formulation according to claim 1, wherein the insulin has the same amino acid sequence as native insulin.

3. The liquid formulation according to claim 1, wherein the insulin is an insulin derivative generated by an amino acid substitution, deletion, or insertion of native insulin.

4. The liquid formulation according to claim 1, wherein the insulinotropic peptide is selected from the group consisting of glucagon like peptide-1 (GLP-1), GLP-2, exendin-3, exendin-4, and a derivative thereof,
   said derivative of the insulinotropic peptide being one selected from the group consisting of:
   a desamino-histidyl derivative in which the N-terminal amino group or amine group of the insulinotropic peptide is deleted;
   a beta-hydroxy imidazopropionyl derivative in which an amino group of the insulinotropic peptide is substituted by hydroxyl group;
   a dimethyl-histidyl derivative in which an amino group of the insulinotropic peptide is modified with two methyl groups;
   a betacarboxyimidazopropionyl derivative in which the N-terminal amino group of the insulinotropic peptide is substituted by carboxyl group; and
   an imidazoacetyl derivative wherein the alpha-carbon of the N-terminal histidine residue of the insulinotropic peptide is deleted.

5. The liquid formulation according to claim 4, wherein the insulinotropic peptide derivative is an imidazoacetyl exendin-4.

6. The liquid formulation according to claim 1, wherein the immunoglobulin Fc region is a Fc region derived from IgG, IgA, IgD, IgE, or IgM.

7. The liquid formulation according to claim 6, wherein the immunoglobulin Fc region is a hybrid of domains from different immunoglobulins selected from the group consisting of IgG, IgA, IgD, IgE, and IgM.

8. The liquid formulation according to claim 6, wherein the immunoglobulin Fc region is a dimer or multimer composed of single-chain immunoglobulins consisting of domains having same origin.

9. The liquid formulation according to claim 6, wherein the immunoglobulin Fc region is IgG4 Fc region.

10. The liquid formulation according to claim 9, wherein the immunoglobulin Fc region is a human aglycosylated IgG4 Fc region.

11. The liquid formulation according to claim 1, wherein the conjugate is linked by using a non-peptidyl polymer or a recombination technique.

12. The liquid formulation according to claim 11, wherein the non-peptidyl polymer is a polyethylene glycol.

13. The liquid formulation according to claim 11, wherein the non-peptidyl polymer is selected from the group consisting of a biodegradable polymer such as a polypropylene glycol, a copolymer of ethylene glycol and propylene glycol, a polyoxyethylated polyol, polyvinyl alcohol, polysaccharide, dextran, polyvinyl ethyl ether, polylactic acid, and polylactic-glycolic acid; a lipid polymer; chitins; a hyaluronic acid; and a combination thereof.

14. The liquid formulation according to claim 1, wherein the concentration of the long-acting insulin conjugate in a pharmaceutically effective amount is 10 mg/ml to 200 mg/ml, and the concentration of long-acting insulinotropic peptide conjugate is 0.5 mg/ml to 150 mg/ml.

15. The liquid formulation according to claim 1, wherein the sugar alcohol is one or more selected from the group consisting of mannitol and sorbitol.

16. The liquid formulation according to claim 15, wherein the concentration of the sugar alcohol is 1% (w/v) to 15% (w/v) based on a total volume of formulation.

17. The liquid formulation according to claim 1, wherein the buffer is citrate buffer, acetate buffer, or phosphate buffer.

18. The liquid formulation according to claim 1, wherein the concentration of the buffer is 5 to 50 mM based on a total volume of formulation.

19. The liquid formulation according to claim 1, wherein the pH range of the buffer is from 5.5 to 7.0.

20. The liquid formulation according to claim 1, wherein the isotonic agent is selected from the group consisting of sodium chloride, sodium sulfate, and sodium citrate.

21. The liquid formulation according to claim 1, wherein the concentration of the isotonic agent is 0.5 mg/ml to 30 mg/ml.

22. The liquid formulation according to claim 1, wherein the non-ionic surfactant is polysorbate or poloxamer.

23. The liquid formulation according to claim 22, wherein the concentration of the non-ionic surfactant is 0.001% (w/v) to 0.05% (w/v).

24. The liquid formulation according to claim 1, wherein the stabilizer further comprises methionine.

25. The liquid formulation according to claim 24, wherein the concentration of the methionine is 0.005% (w/v) to 0.1% (w/v) based on a total volume of formulation.

26. The liquid formulation according to claim 1, wherein the stabilizer further comprises one or more substances selected from the group consisting of sugars, polyalcohol, and amino acids.

27. The liquid formulation according to claim 1, which comprises a long-acting insulin conjugate and long-acting insulinotropic peptide conjugate, in which the insulin and insulinotropic peptide are each linked to an immunoglobulin fragment through polyethylene glycol, and an albumin-free stabilizer, wherein the stabilizer comprises acetate buffer, mannitol, polysorbate 20, and sodium chloride.

28. The liquid formulation according to claim 1, further comprising methionine.

29. A method for preparing the liquid formulation of claim 1, comprising mixing a long-acting insulin conjugate and a long-acting insulinotropic peptide conjugate with a stabilizer comprising a buffer, a sugar alcohol, a non-ionic surfactant, and an isotonic agent,
wherein the long-acting insulin conjugate is in a form in which the insulin is linked to an immunoglobulin Fc region;
wherein the long-acting insulinotropic peptide conjugate is in a form in which the insulinotropic peptide is linked to the immunoglobulin Fc region, and
wherein the buffer has a pH ranging from 5.0 to 7.0.

30. The liquid formulation according to claim 1, wherein the insulinotropic peptide is selected from the group consisting of a desamino-histidylexendin-4; a beta-hydroxy imidazopropionyl-exendin-4; a beta-carboxyimidazopropionyl-exendin-4; a dimethyl-histidyl-exendin-4; and an imidazoacetyl-exendin-4.

* * * * *